(12) United States Patent
Buttermann

(10) Patent No.: US 9,770,275 B2
(45) Date of Patent: Sep. 26, 2017

(54) ORTHOPAEDIC PLATE

(75) Inventor: Glenn R. Buttermann, Mahtomedi, MN (US)

(73) Assignee: Dynamic Spine, LLC, Mahtomedi, MN (US)

( * ) Notice: Subject to any disclaimer, the term of this patent is extended or adjusted under 35 U.S.C. 154(b) by 156 days.

(21) Appl. No.: 13/985,257

(22) PCT Filed: Feb. 13, 2012

(86) PCT No.: PCT/US2012/024862
§ 371 (c)(1),
(2), (4) Date: Oct. 30, 2013

(87) PCT Pub. No.: WO2012/112444
PCT Pub. Date: Aug. 23, 2012

(65) Prior Publication Data
US 2014/0214088 A1 Jul. 31, 2014

Related U.S. Application Data

(60) Provisional application No. 61/442,646, filed on Feb. 14, 2011.

(51) Int. Cl.
*A61B 17/80* (2006.01)
*A61B 17/17* (2006.01)
(Continued)

(52) U.S. Cl.
CPC ...... *A61B 17/8028* (2013.01); *A61B 17/1728* (2013.01); *A61B 17/1757* (2013.01);
(Continued)

(58) Field of Classification Search
CPC . A61B 17/17; A61B 17/1725; A61B 17/1728; A61B 17/7059; A61B 17/8008;
(Continued)

(56) References Cited

U.S. PATENT DOCUMENTS 4,175,555 A * 11/1979 Herbert ................ A61B 17/863
411/415
5,108,399 A * 4/1992 Eitenmuller ....... A61B 17/8047
606/298

(Continued)

FOREIGN PATENT DOCUMENTS

WO WO-2008/064211 A1 5/2008

OTHER PUBLICATIONS

International Preliminary Report on Patentability mailed Aug. 29, 2013, as received in corresponding International Application No. PCT/US2012/024862.

(Continued)

*Primary Examiner* — Anu Ramana
(74) *Attorney, Agent, or Firm* — Foley & Lardner LLP

(57) ABSTRACT

An orthopedic device for repairing a portion of a body comprises an orthopedic plate and a tissue protector. The orthopedic plate is configured to attach to at least one bone. The tissue protector is securely attached to the orthopedic plate and configured to at least partially detach from the orthopedic plate after a force is applied to the tissue protector. The tissue protector includes a thinned region at a portion of the tissue protector proximate to the orthopedic plate. A method of repairing parts of a body with an orthopedic device having an orthopedic plate and a tissue protector securely attached to the orthopedic plate comprises placing the orthopedic plate on at least one bone; fastening a fastener into the tissue protector and then the orthopedic plate; and detaching the tissue protector from the orthopedic plate after the fastener is completely fastened into the tissue protector and the orthopedic plate.

25 Claims, 13 Drawing Sheets

(51) Int. Cl.
  *A61B 17/70* (2006.01)
  *A61B 90/00* (2016.01)
(52) U.S. Cl.
  CPC ...... *A61B 17/7059* (2013.01); *A61B 17/8047* (2013.01); *A61B 17/809* (2013.01); *A61B 2090/037* (2016.02); *F04C 2270/0421* (2013.01)
(58) Field of Classification Search
  CPC ... A61B 17/58; A61B 17/70; Y10T 29/49948; Y10T 29/49954; Y10T 29/49739
  See application file for complete search history.

(56) References Cited

U.S. PATENT DOCUMENTS

| | | | |
|---|---|---|---|
| 5,549,612 A * | 8/1996 | Yapp et al. | 606/293 |
| 5,601,553 A * | 2/1997 | Trebing | A61B 17/15 411/399 |
| 5,709,686 A * | 1/1998 | Talos | A61B 17/8057 606/280 |
| 6,235,034 B1 | 5/2001 | Bray | |
| 6,261,039 B1 * | 7/2001 | Reed | B23P 6/04 411/178 |
| 6,699,253 B2 * | 3/2004 | McDowell | A61B 17/0642 606/80 |
| 7,101,398 B2 * | 9/2006 | Dooris | A61F 2/08 606/151 |
| 7,303,564 B2 | 12/2007 | Freid et al. | |
| 7,357,804 B2 * | 4/2008 | Binder et al. | 606/96 |
| 8,840,677 B2 * | 9/2014 | Kale | A61B 17/686 606/313 |
| 2002/0029040 A1 | 3/2002 | Morrison et al. | |
| 2002/0082606 A1 | 6/2002 | Suddaby | |
| 2005/0070899 A1 | 3/2005 | Doubler et al. | |
| 2005/0228398 A1 | 10/2005 | Rathbun et al. | |
| 2005/0234467 A1 * | 10/2005 | Rains | 606/96 |
| 2006/0084980 A1 | 4/2006 | Melkent et al. | |
| 2006/0149250 A1 | 7/2006 | Castaneda et al. | |
| 2006/0200147 A1 | 9/2006 | Ensign et al. | |
| 2006/0235410 A1 * | 10/2006 | Ralph | A61B 17/686 606/313 |
| 2006/0264962 A1 | 11/2006 | Chin et al. | |
| 2008/0039838 A1 | 2/2008 | Landry et al. | |
| 2009/0012571 A1 | 1/2009 | Perrow et al. | |
| 2009/0157121 A1 | 6/2009 | Harris et al. | |
| 2009/0234392 A1 | 9/2009 | Dziedzic et al. | |
| 2012/0071934 A1 | 3/2012 | Brandon | |

OTHER PUBLICATIONS

International Search Report received in PCT/US2012/024862 dated Jul. 11, 2012.
Patent Examination Report No. 1 dated Aug. 26, 2015, in corresponding Australian application No. 2012217915, 3 pages.
Supplementary European Search Report in corresponding European application No. 12746923.7 dated May 13, 2016, 9 pages.
Extended European Search Report dated Sep. 2, 2016, received in corresponding European application No. 12886871.8, 9 pages.
Office Action dated Jan. 16, 2017, in corresponding European application No. 12 746 923.7, 5 pages.
EPO Examination Report dated May 19, 2017, received in corresponding European application No. 12 746 923.7, 3 pages.

* cited by examiner

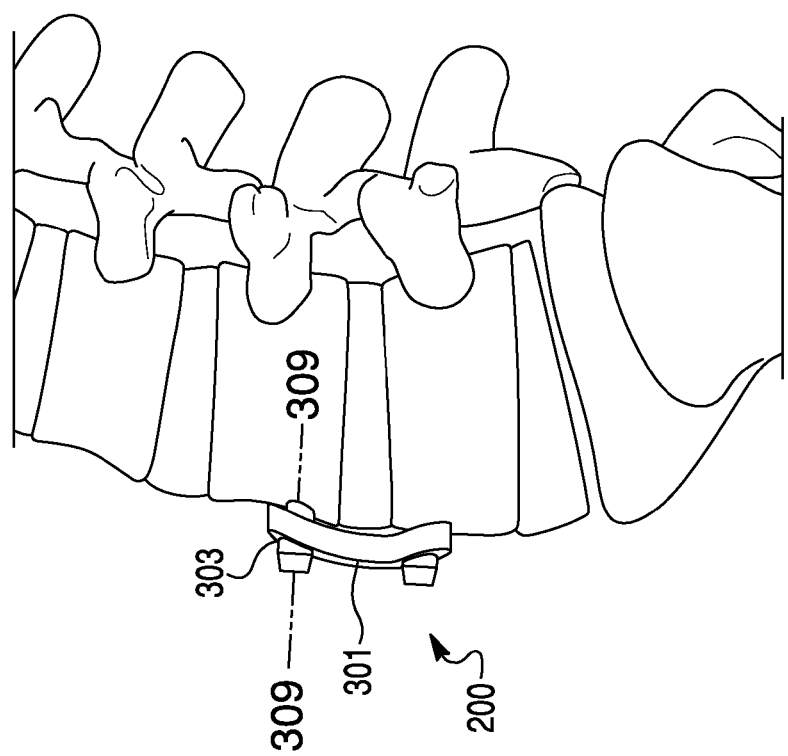
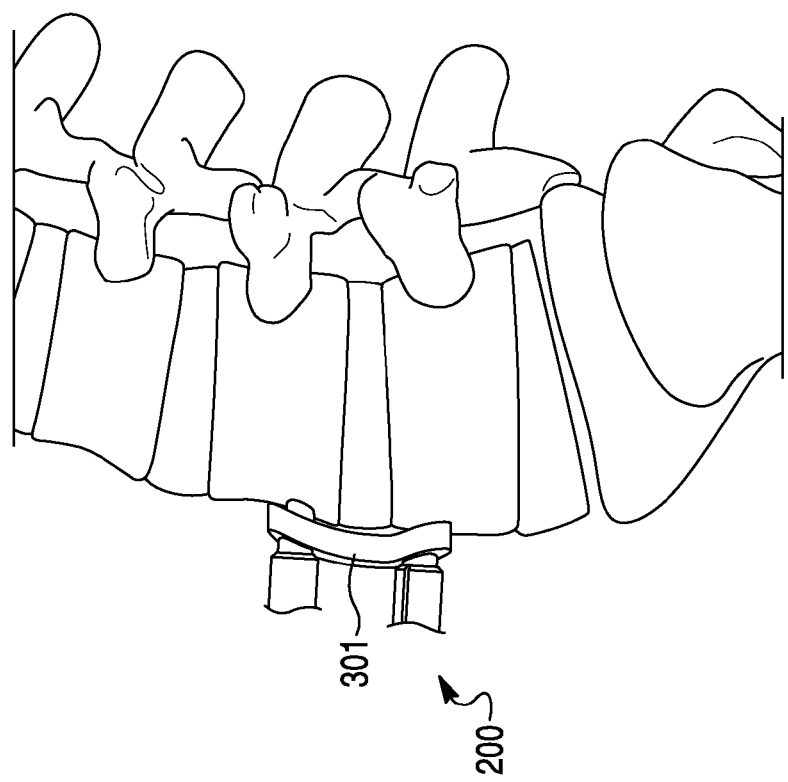

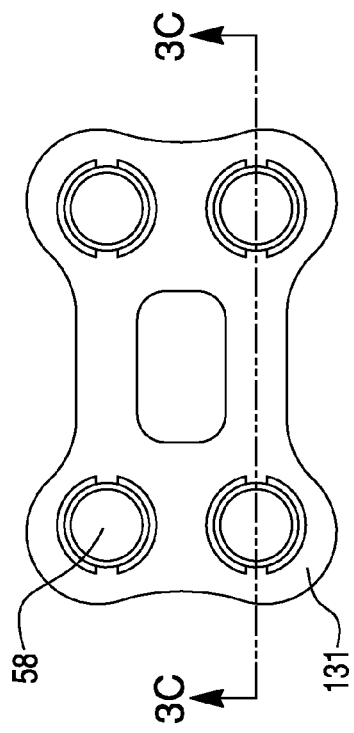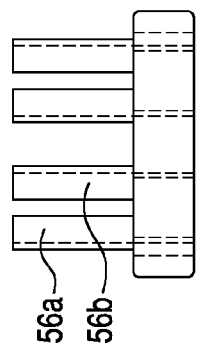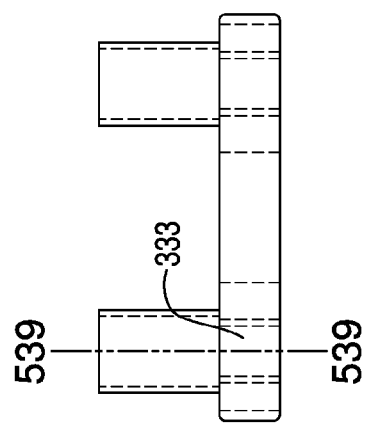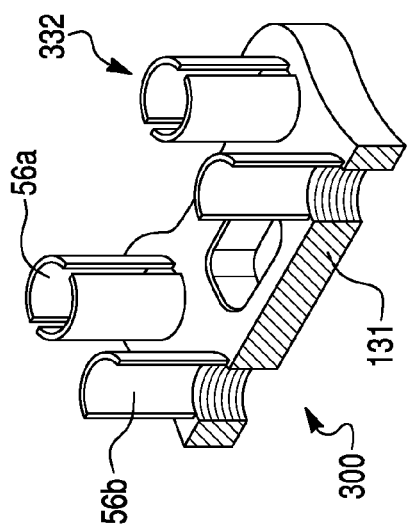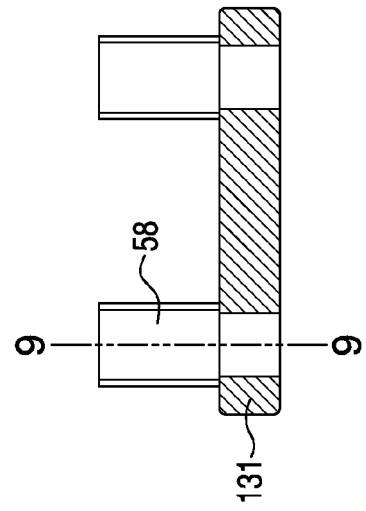

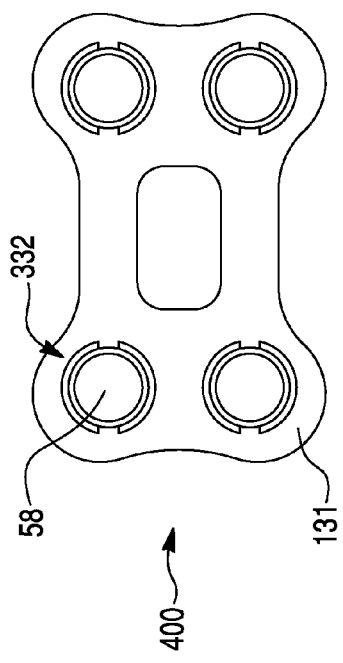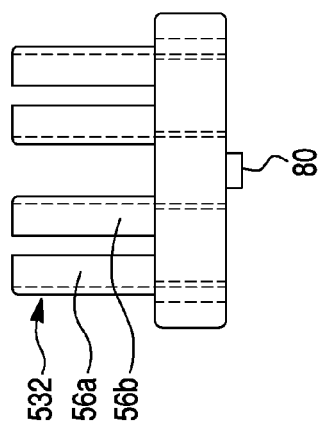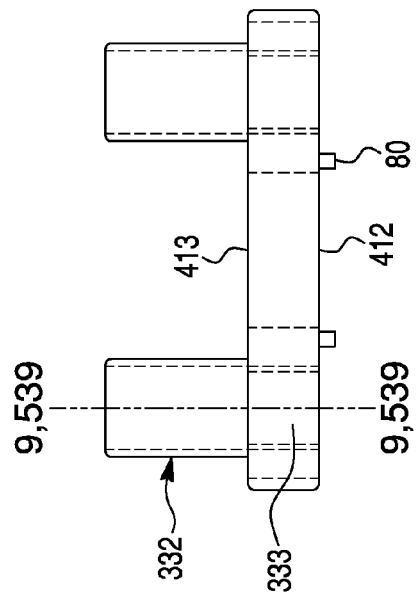

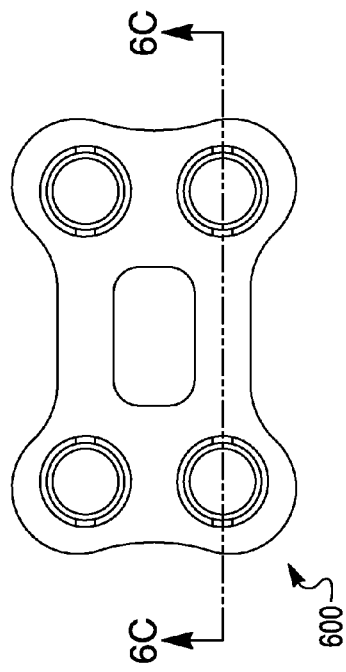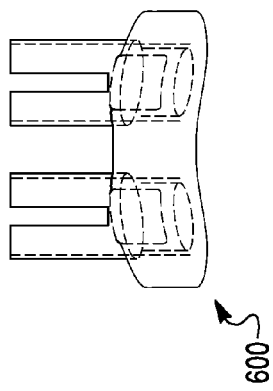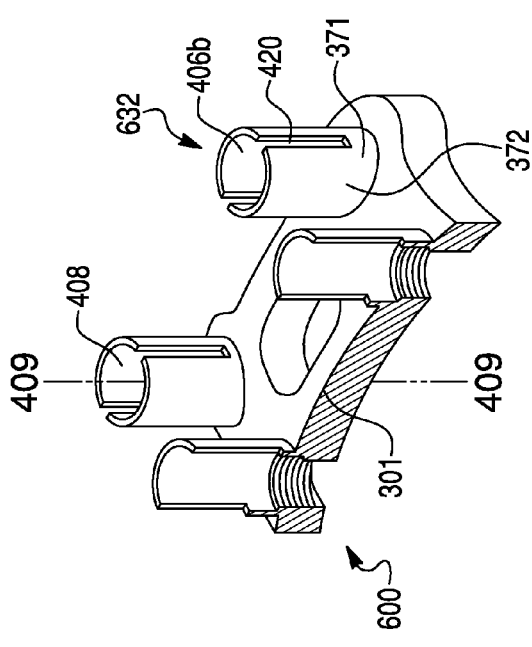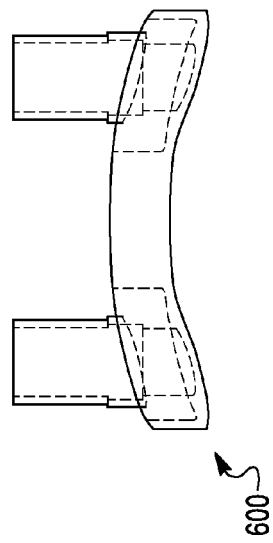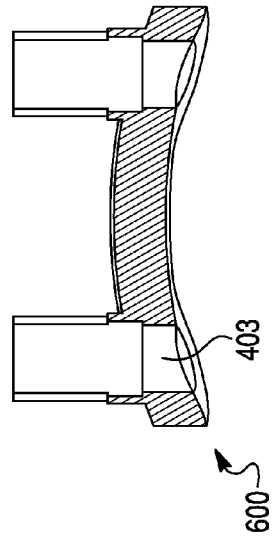

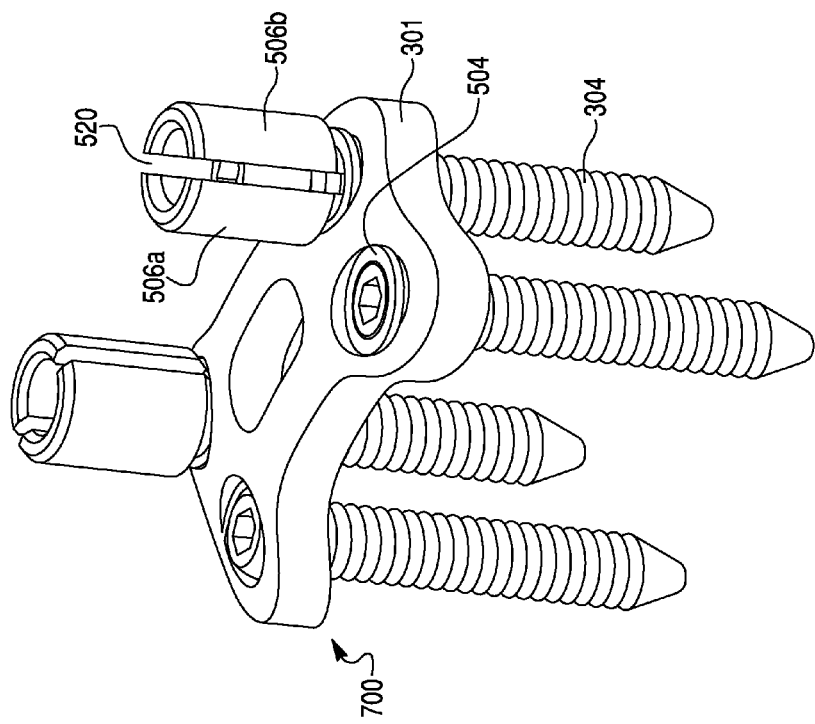

ORTHOPAEDIC PLATE

CROSS REFERENCE TO RELATED APPLICATIONS

The present application is a National Stage of International Application No. PCT/US2012/024862 filed on Feb. 13, 2012, which claims the benefit of U.S. Provisional Application No. 61/442,646 filed on Feb. 14, 2011, the entire disclosures of which are incorporated herein by reference.

BACKGROUND

Field of Embodiments

The disclosed embodiments relate generally to an orthopaedic device having an orthopaedic plate and a tissue protector and to a method for repairing parts of a body with an orthopaedic device.

Description of Related Art

During the repair of bone fractures, one or more orthopaedic devices, each orthopaedic device having an orthopaedic plate and a bone screw, may stabilize adjacent bone fragments relative to one another during the healing process. Similarly, during spinal fusion surgery one or more orthopaedic devices that span adjacent vertebrae, along with an intervening bone graft, may stabilize the spine during the healing process. Typically, the repair or surgery involves holding each orthopaedic plate in a desired location on the adjacent bone fragments or vertebrae and, then, using a drill or an awl making a hole for each screw. In some cases, a tap later creates threads within each hole for the subsequent placement of each screw. In other cases, a self-tapping screw creates the threads.

Conventional orthopaedic devices have an orthopaedic plate with a flat or curved profile and various arrangements and alignments of screw holes. The profile and the arrangement and alignment of screw holes depends on the specific application of the orthopaedic plate. Disadvantages result because, during application of the orthopaedic plate and placement of the screws that fix the orthopaedic plate to the bones or vertebrae, surrounding soft tissue (e.g. muscle, tendon, ligaments, blood vessels) get caught and wind around the drill or screws as the screws advance through the screw holes of the orthopaedic plate. A person applying the orthopaedic plate, such as a surgeon or a surgeon's assistant, may use a tissue retractor to hold the soft tissue away from the orthopaedic plate, drill and screws. However, the use of a tissue retractor is not conducive to a minimally invasive approach, which is intended to cause less injury to the surrounding tissue. Yet additional disadvantages result because use of the tissue retractor is often difficult and unfeasible.

A need exists for improved technology, including technology that may address one or more of the above described disadvantages of conventional orthopaedic devices. For example, a need exists for an orthopaedic device with a "built-in" tissue retractor (e.g. tissue protector).

SUMMARY

According to one embodiment, an orthopaedic device for repairing a portion of a body comprises an orthopaedic plate and a tissue protector. The orthopaedic plate is configured to attach to at least one bone. The tissue protector is securely attached to the orthopaedic plate and configured to at least partially detach from the orthopaedic plate after a force is applied to the tissue protector. The tissue protector includes a thinned region at a portion of the tissue protector proximate to the orthopaedic plate.

According to another embodiment, a method of repairing parts of a body with an orthopaedic device having an orthopaedic plate and a tissue protector securely attached to the orthopaedic plate comprises placing the orthopaedic plate on at least one bone. The method also comprises fastening a fastener into the tissue protector and then the orthopaedic plate and detaching the tissue protector from the orthopaedic plate after the fastener is completely fastened into the tissue protector and the orthopaedic plate.

BRIEF DESCRIPTION OF THE DRAWINGS

These and other features, aspects and advantages of the disclosed embodiments will become apparent from the following description, appended claims and the accompanying exemplary embodiments shown in the drawings, which are briefly described below.

FIG. 2C is a side view of the orthopaedic device of FIG. 2A where fasteners have been fully inserted into the spine.

FIG. 2D is a side view of the orthopaedic device of FIG. 2A where fasteners have been fully inserted into the spine and the tissue protectors are detached from the orthopaedic plate.

FIG. 3A is a side elevated view of a portion of an orthopaedic device having an orthopaedic plate with a flat profile and semi-cylindrically shaped tissue protectors.

FIG. 3B is a top view of an orthopaedic device having an orthopaedic plate with a flat profile and semi-cylindrically shaped tissue protectors.

FIG. 3C is a cross section of the orthopaedic device of FIG. 3B taken along line 3C-3C.

FIG. 3D is a side view of the orthopaedic device of FIG. 3B.

FIG. 3E is a front view of the orthopaedic device of FIG. 3B.

FIG. 5A is a top view of an orthopaedic device having an orthopaedic plate with a flat profile and semi-cylindrically shaped tissue protectors.

FIG. 5B is a side view of the orthopaedic device of FIG. 5A.

FIG. 5C is a front view of the orthopaedic device of FIG. 5A.

FIG. 6A is a side elevated view of a portion of an orthopaedic device having an orthopedic plate with a curved profile and semi-cylindrically shaped tissue protectors.

FIG. 6B is a top view of an orthopaedic device having an orthopedic plate with a curved profile and semi-cylindrically shaped tissue protectors.

FIG. 6C is a cross section of the orthopaedic device of FIG. 6B taken along line 6C-6C.

FIG. 6D is a side view of the orthopaedic device of FIG. 6B.

FIG. 6E is a front view of the orthopaedic device of FIG. 6B.

FIG. 7C is a side elevated view of the orthopaedic device of FIG. 7A with fasteners fully inserted into openings of the orthopaedic plate.

DETAILED DESCRIPTION OF THE EMBODIMENTS

Figure 1:
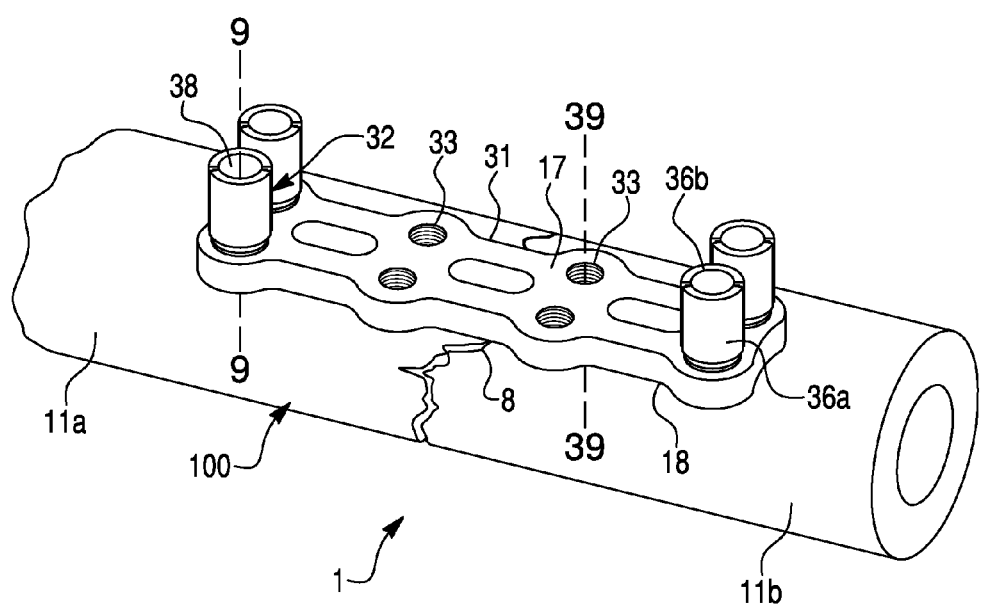
FIG. 1 is a top elevated view of an orthopaedic device having an orthopaedic plate and tissue protectors where the orthopaedic device is attached to a fractured bone.
Figure 2A:
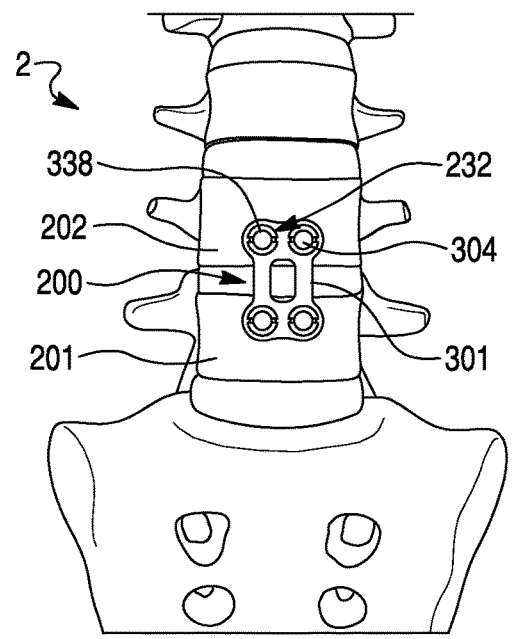
FIG. 2A is a front view of an orthopaedic device having an orthopaedic plate and semi-cylindrically shaped tissue protectors where the orthopaedic device is attached to the spine.
Figure 2B:
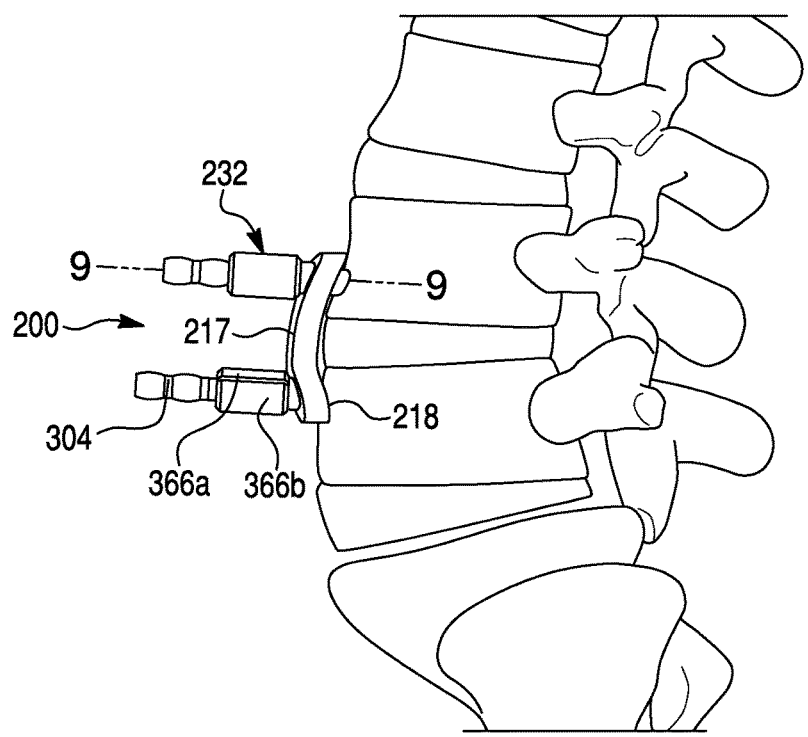
FIG. 2B is a side view of the orthopaedic device of FIG. 2A.

Presently preferred embodiments are illustrated in the drawings. An effort has been made to use the same or like reference numbers throughout the drawings to refer to the same or like parts. The disclosure relates to an orthopaedic device for repairing parts of the body and to a method for repairing parts of a body. The orthopaedic device attaches to a patient's body using minimally invasive procedures so as to protect the patient's soft tissue.

FIGS. 1-12D illustrate embodiments of an orthopaedic device 100, 200, 300, 400, 600, 700, 800, 900, 1000, 1100. The orthopaedic devices 100, 200, 300, 400, 600, 700, 800, 900, 1000, 1100 may be used to facilitate repair a portion of a patient's body. The orthopaedic device 100, 200, 300, 400, 600, 700, 800, 900, 1000, 1100 may include an orthopaedic plate 31, 131, 301, 1101 and a tissue protector 32, 232, 332, 632, 732, 832, 932, 1032, 1132.

The orthopaedic plate 31, 131, 301, 1101 is configured to be attached to at least one bone. For example, the orthopaedic plate 31, 131, 301, 1101 (FIG. 1) may be attached to a first portion 11a and a second portion 11b of a bone segment 1 to facilitate repair of a fracture 8 in the bone segment 1. Alternatively, the orthopaedic plate 31, 131, 301, 1101 (FIGS. 2A-2D) may attach to adjacent vertebrae 201, 202 of a vertebral column 2. The bone may be planar (e.g. flat bones, such as the pelvis, skull, scapula), tubular or other shapes. The aforementioned examples are not intended to be limiting.

The orthopaedic plate 31, 131, 301, 1101 may comprise one or more openings (or holes) 33, 303, 333, 403 that extend through the orthopaedic plate 31, 131, 301, 1101. For example, the orthopaedic plate may have one hole, two holes (FIG. 12), four holes (FIGS. 2A-7D and 10A-10D), six holes (FIG. 1), or some other configuration.

Each hole 33, 303, 333, 403 is configured to receive a fastener 304 (FIGS. 2A-2B, 7A-7C, 8A-8B, 9, 10A-10D and 11). The fastener 304 extends through a hole to attach the orthopaedic plate to a part of the body, such as a bone. A tissue protector 32, 232, 332, 632, 732, 832, 932, 1032, 1132 may be configured to receive the fastener 304. The fastener 304 may be any suitable fastener (e.g. a screw). The fastener may have one thread pitch for a first portion 1256 of the fastener 304 that fits within a part of the body and a different thread pitch for a second portion 1257 of the fastener 304 that fits within the orthopaedic plate 31, 131, 301, 1101 (FIGS. 8A, 9, 10A, 10D and 11). For example, the first portion 1256 of the fastener 304 may have a courser thread than the second portion 1257 of the fastener 304 or the first portion 1256 may have a taper that expands toward the screw head so the threads of the first portion 1256 may cut through a thinned section 371 of the tissue protector 32, 232, 332, 632, 732, 832, 932. In the former example, the differences in thread pitch may provide a lag effect to translate and press the orthopaedic plate 31, 131, 301, 1101 against the part of the body. In contrast, when the thread pitch is the same for the first and second portions 1256, 1257 of the fastener 304, the orthopaedic plate 31, 131, 301, 1101 is not pressed against the part of the body as much as when the thread pitches for the first and second portions 1256, 1257 are different. The first and second portions 1256, 1257 of the fastener 304 may be cylindrically-shaped (FIGS. 7B-7C, 8A-8B, 9, 10A, 10C-10D and 11), conically-shaped or any other suitable shape. Alternatively, one of the first and second portions 1256, 1257 of the fastener 304 may be cylindrically-shaped and the other of the first and second portions 1256, 1257 of the fastener 304 may be conically-shaped. The conically-shaped fastener helps assist in detaching (or shearing off) the tissue protector from the orthopaedic plate.

The holes 33, 303, 333, 403 of the orthopaedic plate 31, 131, 301, 1101 may be positioned anywhere along the orthopaedic plate. When the orthopaedic plate includes holes 403 at just one end (FIG. 12), the orthopaedic plate 1101 may be used as a buttress device such that the orthopaedic plate 1101 may be secured at one end to a bone and the rest of the orthopaedic plate 1101 may span over, but is not secured to, another bone to buttress the bone. For example, the buttressing part of an anteriorly placed spinal plate may be positioned to prevent an adjacent structural bone graft from dislodging anteriorly or to the side. When the orthopaedic plate has multiple holes, the rigidity between the orthopaedic plate 31, 131, 301, 1101 (FIGS. 1-12) and the part(s) of the body to which the orthopaedic plate 31, 131, 301, 1101 attaches increases as the number of holes through which fasteners 304 are fastened increases.

When the orthopaedic plate 31, 131, 301, 1101 has multiple openings, not all of the holes need to be securely attached to a tissue protector. For example, when the orthopedic plate 31 has six holes (FIG. 1), only four of the holes may each be securely attached to a tissue protector. To increase the protection to a patient's soft tissue, preferably at least the holes at the outer four corners of the six hole orthopaedic plate 31 each include a tissue protector 32.

The relative trajectory of the openings 33, 303, 333, 403 (FIGS. 1, 2D, 3D and 10C) may be parallel, converging or diverging such that the opening 33, 303, 333, 403 may one of extend parallel to, diverge from and converge from a longitudinal axis 39-39, 309-309, 539-539 (FIGS. 1, 2D, 3D and 10C) of the hole 33, 303, 333, 403. The trajectory depends on the surface of the body on which the orthopaedic plate 31, 131, 301, 1101 is intended to attach.

The openings 33, 303, 333, 403 may be any suitable size and may comprise threads that mate with the fasteners. For example, the diameter of the holes 33, 303, 333, 403 may range from 3.5 mm to 6 mm. The holes 33, 303, 333, 403 may be threaded by any suitable threading mechanism. For example, the holes 33, 303, 333, 403 may be threaded by a fastener 304 (e.g. a self-threading fastener) or by a threading element (e.g. a tap). Alternatively, the hole 33, 303, 333, 403 may not be threaded.

The orthopaedic plate 131 may comprise a tab 80 (FIGS. 5B-5C) extending from a bottom surface 412 of the orthopaedic plate 131 and configured to insert into one of an opening in the bone and an opening between adjacent bones. The orthopaedic plate 131 may comprise one or more tabs 80. The bottom surface 412 of the orthopaedic plate 131 is opposite to the top surface 413 of the orthopaedic plate 131 and abuts a bone when the orthopaedic plate 131 contacts a bone. The tab 80 decreases the amount of force that each fastener 304 fastened to the orthopaedic plate 131 and the body must share. Preferably, the tab 80 is used to connect to vertebrae where the tab 80 inserts into an intervertebral space. The tab 80 is generally a 1 mm to 3 mm projection that is parallel to the vertebral bony end plate and the tab 80 may be 3 mm wide up the width of the orthopaedic plate.

The orthopaedic plate 31, 131, 1101 may have a flat profile (FIGS. 1 and 3A-5D), a curved profile (FIGS. 2A-2D, 6A-11) or other profile suitable for the intended use. Orthopaedic plates with a flat profile can be placed on a portion of the body having a flat profile. Orthopaedic plates with a curved profile can be placed on a portion of the body having a curved profile. Regardless of the profile of the orthopaedic plate 31, 131, 301, 1101 the orthopaedic plate 31, 131, 301, 1101 may be any suitable width, length and height and may comprise any suitable material. For example, the orthopaedic plate may be 8 mm to 20 mm wide, 25 mm to 150 mm long and 2 mm to 6 mm high. The orthopaedic plate 31, 131, 301, 1101 can be formed, for example, of titanium, stainless steel, cobalt-chrome alloy, carbon fiber, PEEK (Polyether ether ketone) or a composite of these materials.

The tissue protector 32, 232, 332, 632, 732, 832, 932, 1032, 1132 securely attaches (e.g strongly fits) to the orthopaedic plate 31, 131, 301, 1101 and is configured to at least partially detach from the orthopaedic plate 31, 131, 301, 1101 after a force, such as a substantial force, is applied to the tissue protector 32, 232, 332, 632, 732, 832, 932, 1032, 1132. The secure attachment may be any suitable attachment. For example, the secure attachment may be that the tissue protector 32, 232, 332, 632, 732, 832, 932, 1032, 1132 integrally attaches to the orthopaedic plate 31, 131, 301, 1101. The orthopaedic plate 31, 131, 301, 1101 and the tissue protector 32, 232, 332, 632, 732, 832, 932, 1032, 1132 can be integrally attached via any suitable mechanism. For example, the orthopaedic plate 31, 131, 301, 1101 and the tissue protector 32, 232, 332, 632, 732, 832, 932, 1032, 1132 could be machined from a single piece of metal stock and or separate pieces of metal stock. If the orthopaedic plate 31, 131, 301, 1101 and the tissue protector 32, 232, 332, 632, 732, 832, 932, 1032, 1132 are made from separate pieces of metal stock, then they may be welded or shrink fit together at an interface or just below the top surface 17, 217, 317, 1117 of the orthopaedic plate 31, 131, 301, 1101. The top surface 17, 217, 317, 1117 of the orthopaedic plate 31, 131, 301, 1101 is the surface of the orthopaedic plate from which fasteners are first received in the orthopaedic plate 31, 131, 301, 1101 and is distal from a bottom surface 18, 218, 318 of the orthopaedic plate 31, 131, 301, 1101 that is configured to abut the part of the body. Welding may be done by any suitable method of welding (e.g. laser or electro-welding). The tissue protector may also be referred to as a split bushing, blade or sleeve.

Figure 10B:
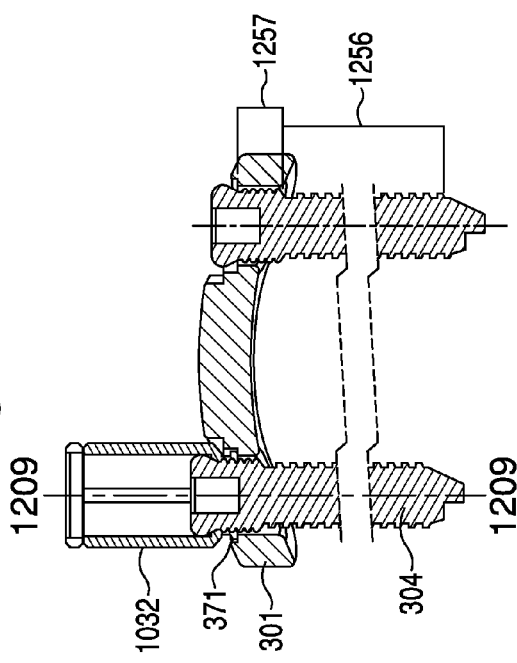
FIG. 10B is a top view of FIG. 10A.
Figure 10D:
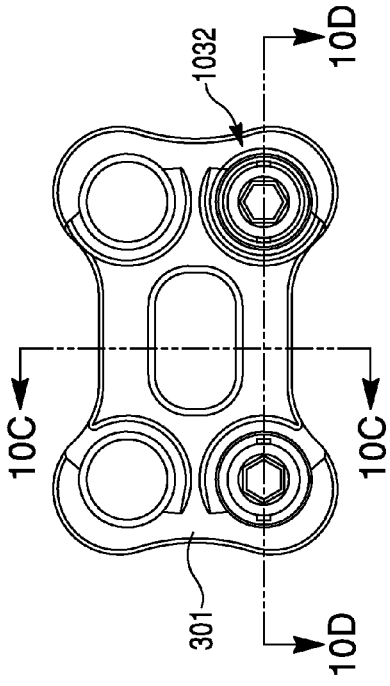
FIG. 10D is a cross section of the orthopaedic device of FIG. 10B taken along line 10D-10D.
Figure 10A:
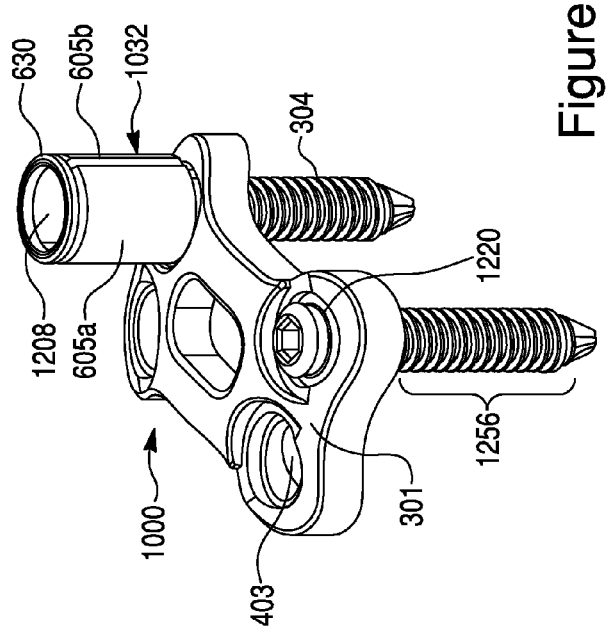
FIG. 10A is a side perspective view of an orthopaedic device having an orthopaedic plate with a curved profile, a semi-cylindrically shaped tissue protector connected to the orthopaedic plate, a semi-cylindrically shaped tissue protector substantially detached from the orthopaedic plate and a connecting band.
Figure 10C:
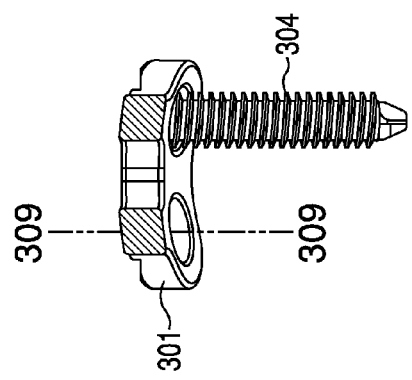
FIG. 10C is a cross section of the orthopaedic device of FIG. 10B taken along line 10C-10C.

There may be one or more tissue protectors 32, 232, 332, 632, 732, 832, 932, 1032, 1132 attached to the orthopaedic plate 31, 131, 301, 1101. For example, four tissue protectors may attach to the orthopaedic plate (FIGS. 1, 3A-3B, 4A-4B, 5A, 6A-6B). Alternatively, two tissue protectors 1132 (FIGS. 10A and 11) may attach to the orthopaedic plate 1101. The number of tissue protectors may equal the number of openings in the orthopaedic plate (FIGS. 3A-3B, 4A-4B, 5A, 6A-6B, 12) or the number of tissue protectors may be less than the number of openings in the orthopaedic plate (FIGS. 1 and 10A).

The tissue protector 32, 232, 332, 632, 732, 832, 932, 1032, 1132 is configured to prevent surrounding tissue from interfering with fixation of the fastener 304 to the orthopaedic plate 31, 131, 301, 1101 or at least reduce negative effects. The tissue protector 32, 232, 332, 632, 732, 832, 932, 1032, 1132 may prevent the top of the fastener 304 and, if the fastener 304 is threaded, its threads from injuring the surrounding tissue, or at least reduce negative effects. Additionally, the tissue protector 32, 232, 332, 632, 732, 832, 932, 1032, 1132 may keep the tissue from wrapping around the fastener 304 when the fastener 304 advances through the opening 33, 303, 333, 403 of the orthopaedic plate 31, 131, 301, 1101 or at least reduce the wrapping of the tissue.

The tissue protector 32, 232, 332, 632, 732, 832, 932, 1032, 1132 may comprise any suitable material. For example, the tissue protectors 32, 232, 332, 632, 732, 832, 932, 1032, 1132 may comprise titanium, stainless steel, cobalt-chrome alloy, carbon fiber, PEEK (Polyether ether ketone) or a composite of these materials.

Each tissue protector 32, 232, 332, 632, 732, 832, 932, 1032, 1132 includes an opening 38, 58, 338, 408, 508, 1208 (FIGS. 1, 2A, 3B-3C, 5A, 6A, 7A and 10A) that extends through the tissue protector 32, 232, 332, 632, 732, 832, 932, 1032, 1132 along a longitudinal axis 9-9, 409-409, 509-509, 1209-1209 (FIGS. 1, 2B, 3C, 5B, 6A, 7A and 10D) of the tissue protector. The opening 38, 58, 338, 408, 508, 1208 extends from the bottom most portion of the tissue protector 32, 232, 332, 632, 732, 832, 932, 1032, 1132 to the top most portion of the tissue protector 32, 232, 332, 632, 732, 832, 932, 1032, 1132. The opening 38, 58, 338, 408, 508, 1208 is sized to allow a fastener 304 to be disposed within the tissue protector 32, 232, 332, 632, 732, 832, 932, 1032, 1132. The opening 38, 58, 338, 408, 508, 1208 may or may not be threaded. If the opening 38, 58, 338, 408, 508, 1208 is threaded, it may be threaded by a fastener 304 (e.g. a self-threading fastener) or by a threading element (e.g. a tap). The threads could be fine or course.

The tissue protector 32, 232, 332, 632, 732, 832, 932, 1032, 1132 may include a thinned section or region 371 (FIGS. 4A, 6A, 8A-8B, 9, 10 and 12D) at a junction 372 (e.g. portion) (FIGS. 6A, 8A, 9, 10) of the tissue protector proximate to the orthopaedic plate. The junction may be between the orthopaedic plate 31, 131, 301, 1101 and the tissue protector 32, 232, 332, 632, 732, 832, 932, 1032, 1132. The thinned section or region 371 may also be referred to as a circumferential notch. The thinned section 371 is positioned adjacent to the orthopaedic plate 31, 131, 301, 1101.

Figure 4B:
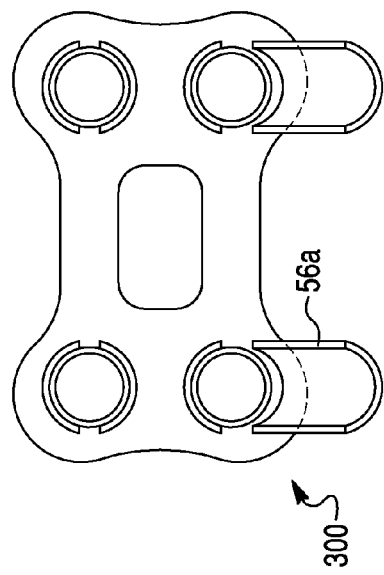
FIG. 4B is a top view of the orthopaedic device of FIG. 4A.
Figure 4D:
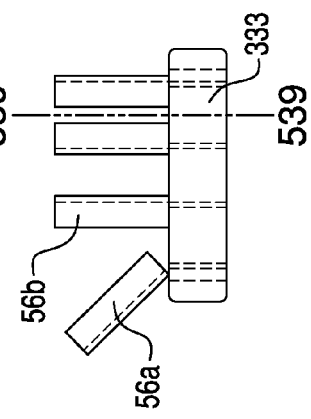
FIG. 4D is a front view of the orthopaedic device of FIG. 4A.
Figure 4A:
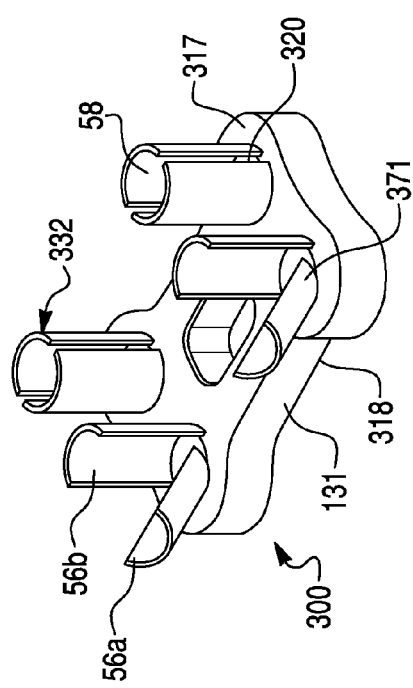
FIG. 4A is a side elevated view of the orthopaedic device of FIG. 3B where some of the tissue protectors are in the process of detaching from the orthopaedic plate.
Figure 4C:
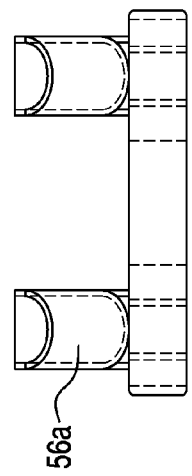
FIG. 4C is a side view of the orthopaedic device of FIG. 4A.
Figure 7B:
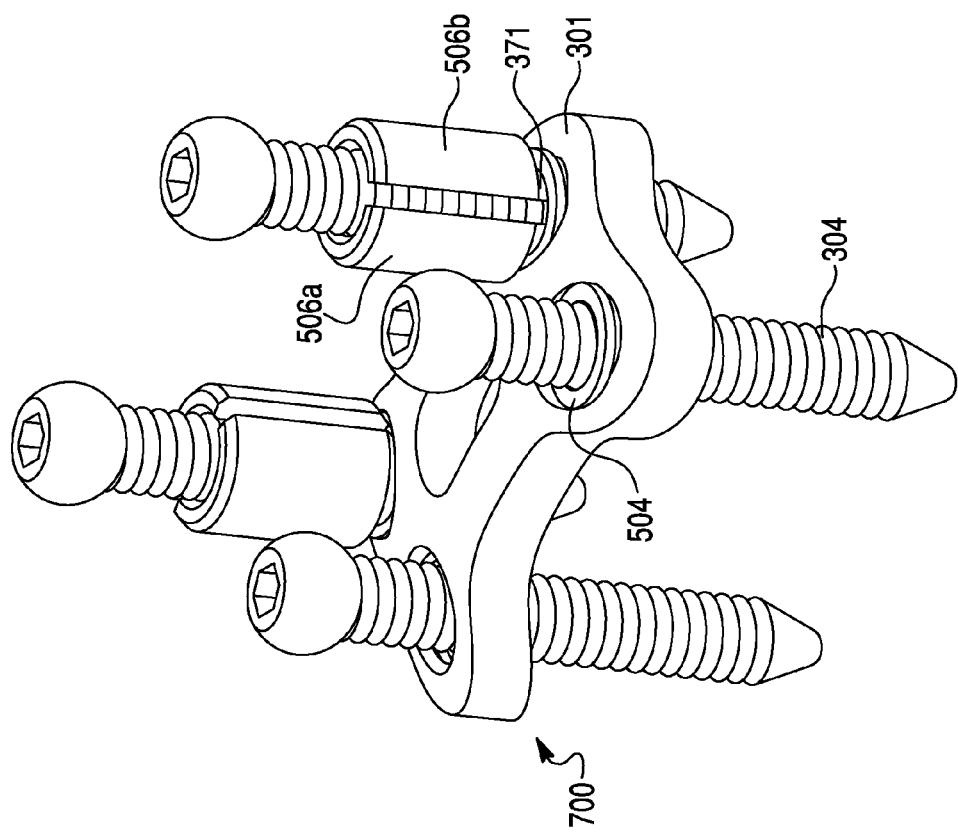
FIG. 7B is a side elevated view of the orthopaedic device of FIG. 7A with fasteners being inserted into openings of the orthopaedic plate.
Figure 7A:
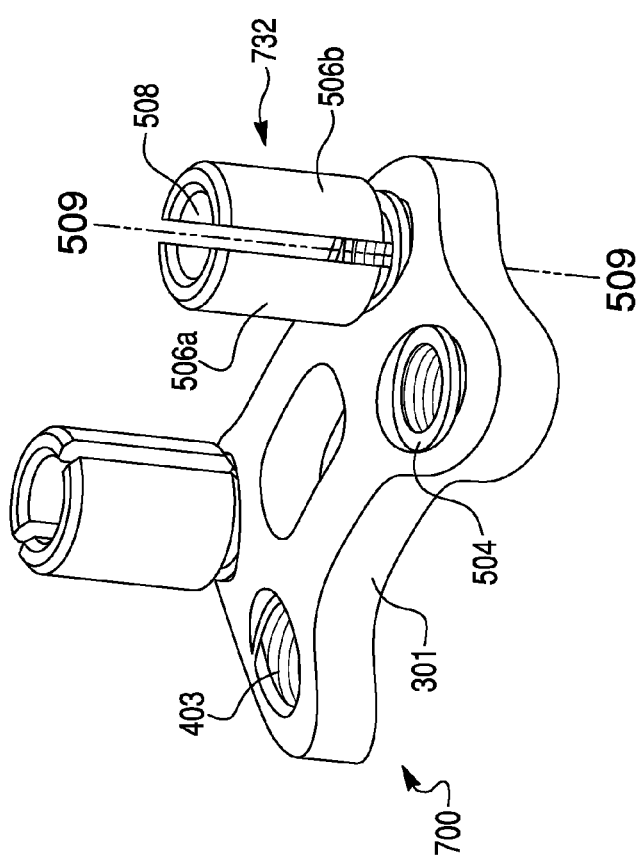
FIG. 7A is a side elevated view of an orthopaedic device having an orthopaedic plate with a curved profile and semi-cylindrically shaped tissue protectors.

The thinned section 371 one of extends continuously and discontinuously around a circumference of the tissue protector 32, 232, 332, 632, 732, 832, 932, 1032, 1132. For example, as shown in FIG. 6A the thinned section 371 may extend around the entire circumference of the tissue protector 632. Alternatively, as shown in FIGS. 3A and 4A the thinned section 371 may be at one or more locations along the circumference of the tissue protector 332.

Figure 8A:
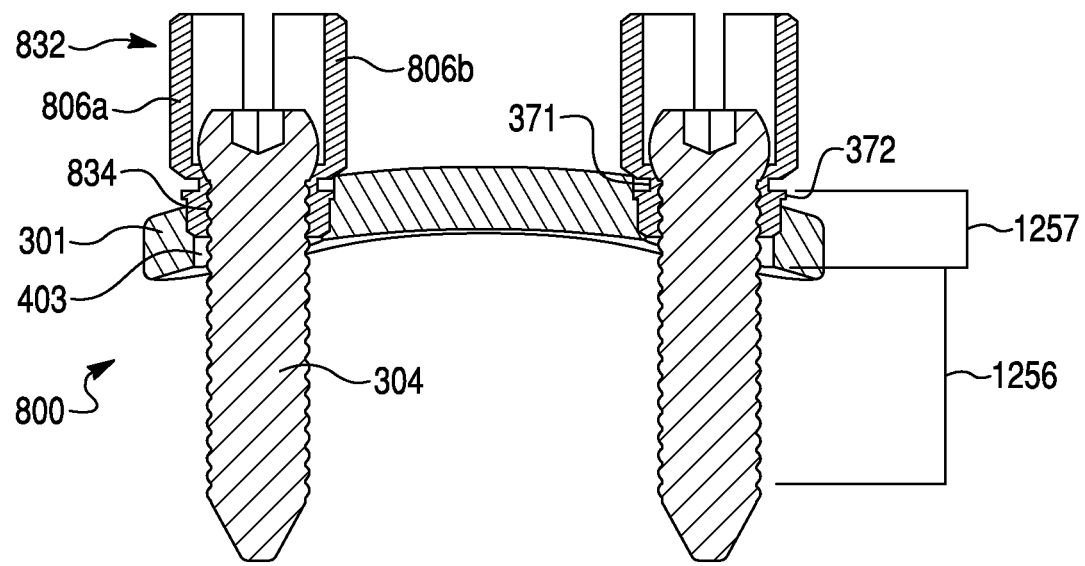
FIG. 8A is a cross-section of an orthopaedic device having an orthopaedic plate with a curved profile and semi-cylindrically shaped tissue protectors.
Figure 8B:
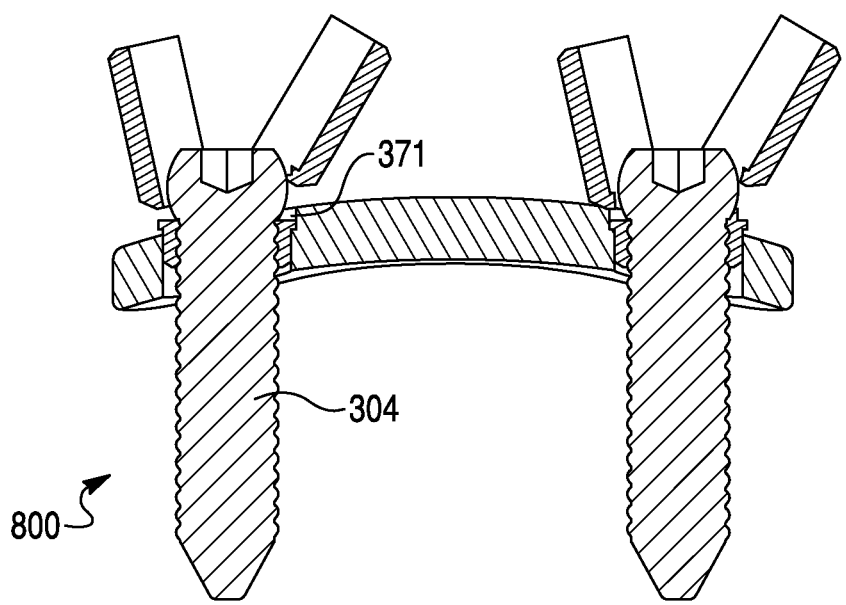
FIG. 8B is a cross-section of the orthopaedic device of FIG. 8A where the semi-cylindrical tissue protectors are in the process of detaching from the orthopaedic plate.
Figure 11:
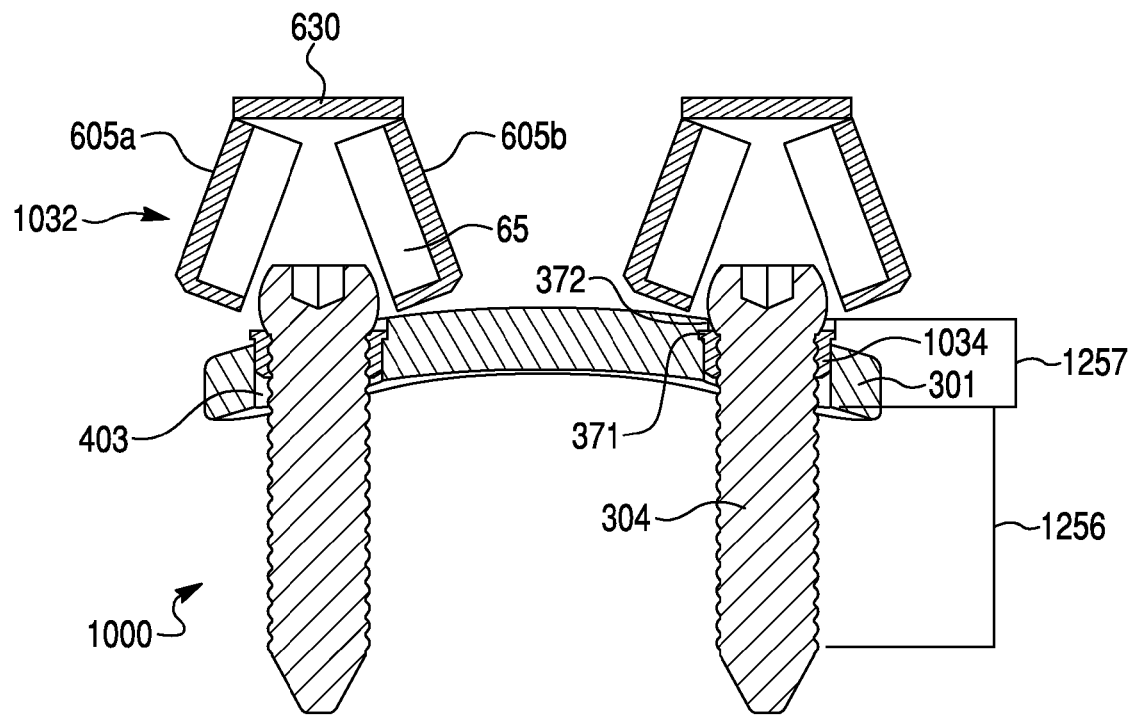
FIG. 11 is a cross-section of an orthopaedic device having an orthopaedic plate with a curved profile and semi-cylindrically shaped tissue protectors which include a connecting band and are in the process of detaching from the orthopaedic plate.
Figure 12:
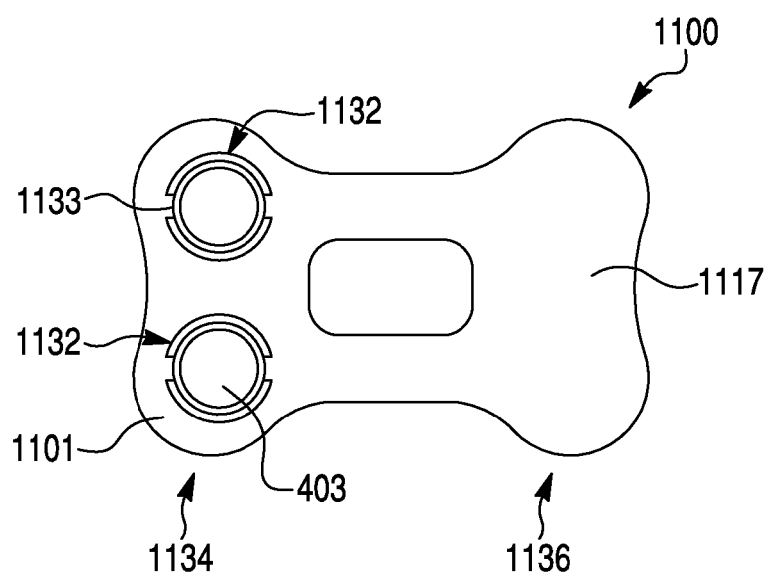
FIG. 12 is a top view of an orthopaedic device having an orthopaedic plate and tissue protectors.

The thinned section 371 is configured to cause the tissue protectors 32, 232, 332, 632, 732, 832, 932, 1032, 1132 to at least partially detach from the orthopaedic plate 31, 131, 301, 1101 when the force is applied to the thinned section 371. The thinned section 371 is able to cause the tissue protectors 32, 232, 332, 632, 732, 832, 932, 1032, 1132 to at least partially detach from the orthopaedic plate 31, 131, 301, 1101 when the force is applied to the thinned section 371 because the thinned section 371 has a thinner width than the remainder of the tissue protector 32, 232, 332, 632, 732, 832, 932, 1032, 1132 and/or a smaller outer diameter than the remainder of the tissue protector 32, 232, 332, 632, 732, 832, 932, 1032, 1132. The thinned section 371 causes substantially all or the entirety of each tissue protector 32, 232, 332, 632, 732, 832, 932, 1032, 1132 to detach from or shear off of the orthopaedic plate 31, 131, 301, 1101 when the suitable force is applied to the thinned section. FIGS. 7C, 8B and 11 show a tissue protector 532, 732, 932, 1032 when a substantial portion 66a, 504, 934, 1034 of the tissue protector 532, 732, 932, 1032 has detached from the orthopaedic plate 301. FIG. 2D shows a tissue protector 232 where all of the tissue protector 232 is detached from the orthopaedic plate 301 and FIG. 10A shows a tissue protector 1032 where one has not detached while the other has substantially detached from the orthopaedic plate 301 such that only a portion 1220 of the tissue protector 1032 remains. The fastener 304 may be fully advanced in the orthopaedic plate 31, 131, 231, 301 and the tissue protector 32, 232, 332, 432, 532, 632, 732, 832, 932, 1032 may still be in the orthopaedic plate, but when the fastener 304 is fully tightened a suitable force is applied to the tissue protector 32, 232, 332, 432, 532, 632, 732, 832, 932, 1032 such that the tissue protector 32, 232, 332, 432, 532, 632, 732, 832, 932, 1032 detaches from the orthopaedic plate.

The tissue protector 32, 232, 332, 432, 532, 632, 732, 832, 932, 1032 may include a first leaf 36a, 56a, 366a, 406a, 506a, 505a, 605a, 806a and a second leaf 36b, 56b, 366b, 406b, 506b, 505b, 605b, 806b (FIGS. 1, 2B, 3A, 4A, 5C, 6A, 7A, 8A, 9, 10A, 10D and 11). The leaves 36a, 36b, 56a, 56b, 366a, 366b, 406a, 406b, 506a, 506b, 505a, 505b, 605a, 605b, 806a, 806b may connect to the orthopaedic plate 31, 131, 301, 1101. Although the figures show each tissue protector 32, 232, 332, 632, 732, 832, 932, 1032, 1132 having two leaves 36a, 36b, 56a, 56b, 366a, 366b, 406a, 406b, 506a, 506b, 505a, 505b, 605a, 605b, 806a, 806b each tissue protector 32, 232, 332, 632, 732, 832, 932, 1032 may have more than two leaves.

The first leaf 36a, 56a, 366a, 406a, 506a, 505a, 605a, 806a and the second leaf 36b, 56b, 366b, 406b, 506b, 505b, 806b may extend from the thinned region 371 and are positioned farther from the orthopaedic plate 31, 131, 301, 1101 than the thinned region 371 is from the orthopaedic plate 31, 131, 301, 1101. The positioning of the leaves 36a, 36b, 56a, 56b, 366a, 366b, 406a, 406b, 506a, 506b, 505a, 505b, 605a, 605b, 806a, 806b with respect to the thinned region 371 is such that the thinned region 371 separates the leaves 36a, 36b, 56a, 56b, 366a, 366b, 406a, 406b, 506a, 506b, 505a, 505b, 605a, 605b, 806a, 806b from the orthopaedic plate 31, 131, 301, 1101.

The first leaf 36a, 56a, 366a, 406a, 506a, 505a, 605a, 806a may connect to the second leaf 36b, 56b, 366b, 406b, 506b, 505b, 806b at the thinned region 371 when the thinned region 371 extends continuously around the circumference of the tissue protector (FIG. 6A) or the first leaf 36a, 56a, 366a, 406a, 506a, 505a, 605a, 806a may be separate from the second leaf 36b, 56b, 366b, 406b, 506b, 505b, 605b, 806b when the thinned region 371 extends discontinuously around the circumference of the tissue protector, such that the first and second leaf do not connect to each other (FIGS. 3A and 4A). When the leaves connect to one another the leaves are stronger, such that the leaves will not detach from the orthopaedic plate until a force is applied (e.g. a substantial/suitable force is applied). In other words, the leaves will not detach from the orthopaedic plate inadvertently (e.g. prior to the fasteners being fully advanced into the orthopaedic plate) When the force is applied to each leaf, the leaf detaches from the orthopaedic plate. At least a portion of the first leaf 36a, 56a, 366a, 406a, 506a, 505a, 605a, 806a may be disconnected from a portion of the second leaf 36a, 56a, 366a, 406a, 506a, 505a, 605a, 806a Alternatively, all of the first leaf may connect to all of the second leaf.

The leaves 36a, 36b, 56a, 56b, 366a, 366b, 406a, 406b, 506a, 506b, 505a, 505b, 605a, 605b, 806a, 806b may have varying orientations (FIGS. 9 and 10) and widths for the space 320, 420, 520 (FIGS. 4A, 6A, 7C) between adjacent leaves. The width for the space 320, 420, 520 between adjacent leaves may range from 0.5 mm to 5 mm, such as between 1 mm to 5 mm.

The tissue protector 32, 232, 332, 632, 732, 832 may comprise one of a substantially conical shape (FIG. 9), substantially cylindrical shape (FIGS. 1-8B, 10A, 10D and 11) or any other shape suitable for the intended use. The diameter of the tissue protectors 932 that are semi-conically shaped increase as the tissue protector 932 gets farther away from where the tissue protector 932 and the orthopaedic plate 301 integrally attach. The minimum and maximum diameter as well as the height of the semi-conically shaped tissue protectors 932 may vary. For example, the outer diameter of the tissue protectors 932 may range from 4 mm to 12 mm (for example, from 4 mm to 8 mm or 6 mm to 12 mm), the inner diameter may range from 4.5 mm to 11.5 mm (for example, from 4.5 mm to 7.5 mm or 6.5 mm to 11.5 mm) and the height may range from 4 mm to 15 mm. Each of the semi-conically shaped tissue protectors 932 allows for a slightly oversized screw head to fit into the opening of the tissue protector 932. The semi-cylindrically shaped tissue protectors 32, 232, 332, 632, 832, 1032 may have varying diameters and heights. For example, the diameter of the tissue protectors 32, 232, 332, 632, 832, 1032 may range from 4 mm to 12 mm (for example, from 4 mm to 8 mm or 6 mm to 12 mm), the inner diameter may range from 4.5 mm to 11.5 mm (for example, from 4.5 mm to 7.5 mm or 6.5 mm to 11.5 mm) and the height from 4 mm to 15 mm.

Figure 9:
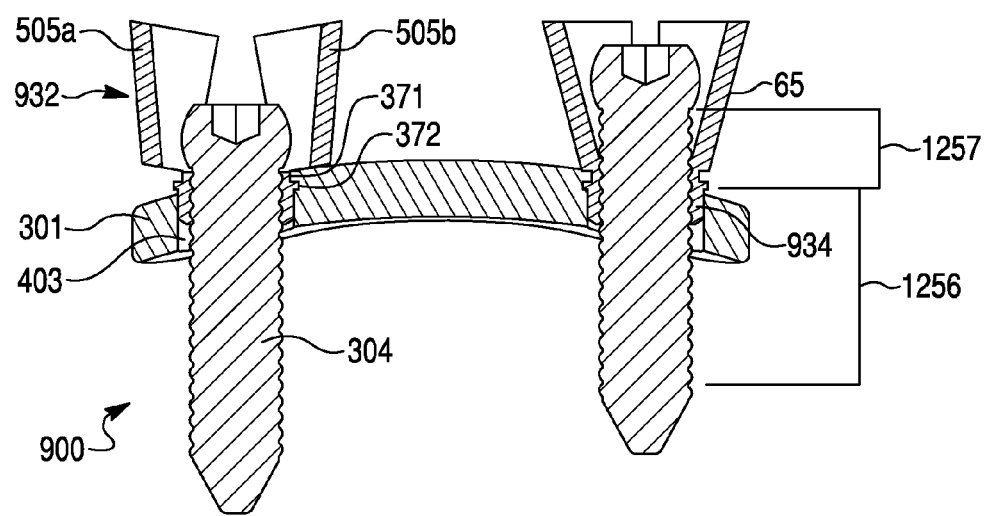
FIG. 9 is a cross-section of an orthopaedic device having an orthopaedic plate with a curved profile and semi-conically shaped tissue protectors, where one of the tissue protectors is in the process of detaching.

Although the semi-conically shaped tissue protectors 932 shown in FIG. 9, are integrally attached to a orthopaedic plate 301 with a curved profile, the semi-conically shaped tissue protectors 932 may integrally attach to an orthopaedic plate with a flat profile. Although, the figures show an orthopaedic plate with all semi-cylindrically shaped tissue protectors or all semi-conically shaped tissue protectors, an orthopaedic plate may have semi-cylindrically and semi-conically shaped tissue protectors. Although, the internal diameter of the tissue protectors 32, 232, 332, 632, 832, 932, 1032 is shown as being constant or substantially constant, the tissue protector may include a varying internal diameter.

The tissue protector 1032 may connect to a connecting band 630 (or collar or top plate) that connects the first leaf 605a to the second leaf 605b (FIGS. 10A and 11) at a position distal from where the tissue protector 1032 attaches to the orthopaedic plate 301. The tissue protector 1032 may be integrally connected to the collar 630 via any suitable mechanism. For example, the tissue protector 1032 and the collar 630 may be formed from the same sheet or the tissue protector 1032 and the collar 630 may be welded together. The connecting band 630 may connect the leaves 605a, 605b of the tissue protector 1032 together at the top portion of the tissue protector 1032. The top plate 630 may include an opening (not shown) through which the fastener 304 can fit.

The collar 630 is configured to hold the tissue protector 1032 together after the tissue protector 1032 is detached or sheared off from the orthopaedic plate 301. The collar 630 may also interact with a screw-driver when the fastener 304 is fastened (e.g. screwed) into the tissue protector 1032 so that, as the fastener 304 is tightened, the tissue protector shears off of the orthopaedic plate and the collar holds to the screw-driver so that the detached tissue protector may be easily retrieved. The top plate 630 prevents the leaves 605a, 605b from displacing from one another at the top end (e.g. end closest to where the fastener 304 enters the top plate 630) while the leaves 605a, 605b detach from the orthopaedic plate. The top plate 630 may have any suitable shape and may connect to any shaped tissue protector. For example, the top plate 630 may be ring-shaped (e.g. circular shaped) and the top plate 630 may connect to leaves of a semi-cylindrically shaped tissue protector (FIGS. 10A and 11) or semi-conically shaped tissue-protector.

A small elastomeric ring (e.g. an O-ring) may be placed at the outer bottom of one or more of the tissue protectors so that when the leaves are detached, there will be a barrier from potential sharp edges of the leaves at the detachment site. The elastomeric ring may be integrally attached to the tissue protector or separate from the tissue protector. Alternatively, a remaining portion 1220 (FIG. 10A) of the tissue protector 1032 may remain after a substantial portion of the leaves are detached so that there will be a barrier from potential sharp edges of the leaves at the detachment site. The remaining portion 1220 is attached to the orthopaedic plate 31, 131, 301, 1101. While the portion 1220 is only shown in the tissue protector 1032 of FIG. 10A, the portion may be part of any tissue protector. The remaining portion 1220 may be at a portion of the tissue protector proximate to the orthopaedic plate 31, 131, 301, 1101.

A method for repairing parts of a body with an orthopaedic device 100, 200, 300, 400, 600, 700, 800, 900, 1000, 1100 having an orthopaedic plate 31, 131, 301, 1101 and a tissue protector 32, 232, 332, 632, 732, 832, 932, 1032 securely attached to the orthopaedic plate 31, 131, 301, 1101 may include first placing the orthopaedic plate 31, 131, 301, 1101 on the part of the body. The part of the body may be at least one bone. An awl (e.g. punch awl) may be used to place the orthopaedic plate 31, 131, 301, 1101 on the part of the body. The awl is able to fit within the openings of the orthopaedic plate and the openings of the tissue protector where the tissue protector may act as a guide for the awl. Instead of an awl, a drill or pin may be used to place the orthopaedic plate 31, 131, 301, 1101 on the part of the body and, like the awl, the drill and pin are able to fit within the openings of the orthopaedic plate and the openings of the tissue protector where the tissue protector may act as a guide for the drill or pin. The tissue protectors may also act as a guide for a drill or a tap that may be used to prepare a hole in at least one bone for receiving the fastener.

Before or after positioning the orthopaedic plate 31, 131, 301, 1101 on the part of the body, each opening 33, 303, 333, 403 of the orthopaedic plate 31, 131, 301, 1101 may or may not be threaded using any suitable mechanism (e.g. manually or automatically). One or more fasteners 304 are fastened into the tissue protector(s) 32, 232, 332, 632, 732, 832, 932, 1032 and then the orthopaedic plate 31, 131, 301, 1101. Each of the fasteners 304 may be fastened by fastening (e.g. screwing) the fastener 304 into one of the tissue protectors 32, 232, 332, 632, 732, 832, 932, 1032 and the orthopaedic plate 31, 131, 301, 1101. The fastener 304 is fastened to the orthopaedic plate 31, 131, 301, 1101 by being inserted into the opening 38, 58, 338, 408, 508 of the tissue protector 32, 232, 332, 632, 732, 832, 932, 1032 and once inserted, fastening to the tissue protector 32, 232, 332, 632, 732, 832, 932, 1032 and then to the orthopaedic plate 31, 131, 301, 1101.

A substantial portion or all of the tissue protectors 32, 232, 332, 632, 732, 832, 932, 1032 may detach from the orthopaedic plate 31, 131, 231, 301 when a force, such as a substantial force, is applied to the tissue protector(s) 32, 232, 332, 632, 732, 832, 932, 1032 by a clamp and/or another suitable mechanism, such as a cylindrical device, a shearing device, or a fastener. Specifically, the tissue protector(s) 32, 232, 332, 632, 732, 832, 932, 1032 detach when the force is applied or exerted on the thinned section 371 by a clamp and/or another suitable mechanism, such as a cylindrical device, a shearing device, or a fastener. The force is preferably not applied until after the fastener 304 is completely fastened to the orthopaedic plate 31, 131, 301, 1101 and the relevant portion of the body.

The force may be exerted by using a clamp to grab an individual leaf 36a, 36b, 56a, 56b, 366a, 366b, 406a, 406b, 506a, 506b, 505a, 505b, 605a, 605b and, after grabbing the leaf, bending or twisting the leaf 36a, 36b, 56a, 56b, 366a, 366b, 406a, 406b, 506a, 506b, 505a, 505b, 605a, 605b until enough force has been exerted on the thinned section 371 to cause the leaf to detach from the orthopaedic plate. In addition to bending and/or twisting (rotating), one can place a cylindrical device inside the tissue protector that can radially expand outward to shear the leaves off at the thinned section 371 or notched region. Outward expansion may be due to advancement of a device through the tissue protector that has a larger diameter than the inner diameter of the tissue protector at its thinned section. Tissue protector detachment by shearing may also be performed by rotation about the hole axis (i.e. the longitudinal axis of the tissue protector). This device may be combined with a clamp to retrieve the leaves from the surgical field. The leaves 36a, 36b, 56a, 56b, 366a, 366b, 406a, 406b, 506a, 506b, 505a, 505b, 605a, 605b may be detached from the orthopaedic plate at different times or simultaneously. The force may also be exerted by a fastener whose threads exert a force on the leaves by cutting through a thinned section of the tissue protector.

In the case of a semi-conically shaped tissue protector 932 the suitable force may be exerted by a slightly oversized fastener head. A slightly oversized fastener head may be one that has a slightly larger diameter than the opening of the tissue protector. When a slightly oversized fastener head fits into the opening (not shown) of the tissue protector 932 and advances through the tissue protector 932 and into the orthopaedic plate 301, the fastener head abuts the inside aspect of a narrower (smaller inner diameter near the orthopaedic plate) portion 65 (FIG. 9A) of the tissue protector 932 just before the fastener 304 is fully seated. The interaction between the narrower portion 65 of the tissue protector 932 and the fastener 304 causes the thinned section 371 to shear away from the orthopaedic plate 301. While a slightly oversized fastener head is discussed in terms of being used for a semi-conically shaped tissue protector, the slightly oversized fastener head may be used for other shaped tissue protectors (e.g. semi-cylindrically shaped tissue protector).

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the construction and arrangement of the orthopaedic device as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosure herein. For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes and omissions may be made in the design, operating conditions and arrangement of the exemplary embodiments.

What is claimed is:

1. An orthopaedic device for repairing a portion of a body, the orthopaedic device comprising:
    an orthopaedic plate configured to attach to at least one bone;
    a fastener for fastening the orthopaedic device; and
    a tissue protector securely attached to the orthopaedic plate,
    wherein the tissue protector includes a detachable portion and a remaining portion,
    wherein the tissue protector includes a thinned region at a portion of the tissue protector proximate to the orthopaedic plate,
    wherein an outer width of a head of the fastener is smaller than an inner width of the detachable portion,
    wherein the outer width of the head of the fastener is larger than an inner width of the thinned region of the tissue protector,
    wherein the detachable portion is configured to detach from the orthopaedic plate and the remaining portion when the fastener is inserted into the tissue protector and the head of the fastener applies a force to the thinned region of the tissue protector while the fastener is tightened to attach the orthopaedic plate to the at least one bone, the remaining portion remaining attached to the orthopaedic plate after the detachable portion is detached,
    wherein the tissue protector includes an opening extending completely through the tissue protector along a longitudinal axis of the tissue protector.

2. The orthopaedic plate of claim 1, wherein the orthopaedic plate comprises an opening that extends through the orthopaedic plate.

3. The orthopaedic plate of claim 2, wherein the opening comprises threads.

4. The orthopaedic plate of claim 2, wherein a longitudinal axis of the opening one of extends parallel to, diverges from, and converges from a longitudinal axis of the orthopaedic plate.

5. The orthopaedic plate of claim 1, wherein the orthopaedic plate comprises a tab extending from a bottom surface of the orthopaedic plate and configured to insert into one of an opening in the bone and an opening between adjacent bones.

6. The orthopaedic plate of claim 1, wherein the thinned region one of extends continuously and discontinuously around a circumference of the tissue protector.

7. The orthopaedic plate of claim 1, wherein the thinned region is configured to cause the detachable portion of the tissue protector to detach from the orthopaedic plate when the force is applied.

8. The orthopaedic plate of claim 1, wherein the thinned region is configured to cause the detachable portion of the tissue protector to detach from the orthopaedic plate when cut by fastener threads.

9. The orthopaedic plate of claim 1,
wherein the detachable portion comprises a first leaf and a second leaf, and
wherein the first and second leaves extend from the thinned region and are positioned farther from the orthopaedic plate than the thinned region.

10. The orthopaedic plate of claim 9, wherein the first leaf connects to the second leaf at the thinned region when the thinned region extends continuously around the circumference of the tissue protector.

11. The orthopaedic plate of claim 9, wherein the first leaf is separate from the second leaf when the thinned region extends discontinuously around the circumference of the tissue protector.

12. The orthopaedic plate of claim 9, further comprising a connecting band that connects the first leaf to the second leaf at a position distal from where the tissue protector attaches to the orthopaedic plate.

13. The orthopaedic plate of claim 12, wherein the connecting band includes an opening.

14. The orthopaedic plate of claim 1, wherein the tissue protector comprises one of a substantially conical and cylindrical shape.

15. The orthopaedic plate of claim 1, wherein the fastener is configured to attach the orthopaedic plate to the bone, wherein the orthopaedic plate and the tissue protector are configured to receive the fastener, wherein the fastener is configured to attach to the at least one bone.

16. The orthopaedic plate of claim 1, wherein the remaining portion is configured to be attached to the orthopaedic plate by the fastener and wherein the remaining portion abuts the orthopaedic plate.

17. The orthopaedic plate of claim 1, wherein the tissue protector is integrally attached to the orthopaedic plate.

18. The orthopaedic plate of claim 1, wherein the tissue protector and the orthopaedic plate are configured to receive at least one of a drill, awl and pin.

19. The orthopaedic plate of claim 1, wherein the tissue protector further includes a varying internal diameter.

20. The orthopaedic plate of claim 1, wherein the orthopaedic plate has a top surface and a bottom surface, wherein the bottom surface is configured to abut the at least one bone, wherein the tissue protector does not extend beyond the bottom surface.

21. The orthopaedic plate of claim 1, wherein the fastener is configured to attach the orthopaedic plate to the at least one bone by directly attaching to the at least one bone.

22. The orthopaedic plate of claim 1, wherein the detachable portion of the tissue protector has a smooth outer circumference.

23. A method of repairing parts of a body with an orthopaedic device having an orthopaedic plate and a tissue protector securely attached to the orthopaedic plate, the method comprising:

placing the orthopaedic plate on at least one bone;

fastening a fastener into the tissue protector and then the orthopaedic plate; and detaching a detachable portion of the tissue protector from the orthopaedic plate and a remaining portion of the tissue protector with the fastener that is inserted into the tissue protector and applies a force to the tissue protector while the fastener is tightened to attach the orthopaedic plate to the at least one bone, wherein the detachable portion is detached after the fastener is completely fastened with the remaining portion of the tissue protector and into the orthopaedic plate, the remaining portion remaining attached to the orthopaedic plate after the detachable portion is detached, wherein the tissue protector includes an opening extending completely through the tissue protector along a longitudinal axis of the tissue protector.

24. The method of claim 23, further comprising applying a force to the tissue protector to detach the detachable portion of the tissue protector from the orthopaedic plate.

25. The method of claim 23, further comprising a fastener for fastening the orthopaedic device, wherein an outer width of a head of the fastener is smaller than an inner width of the detachable portion, wherein the outer width of the head of the fastener is larger than an inner width of the thinned region of the tissue protector, wherein the head of the fastener applies a force to the thinned region of the tissue protector to detach the detachable portion of the tissue protector.

* * * * *